US007357777B1

(12) United States Patent
Meyers

(10) Patent No.: US 7,357,777 B1
(45) Date of Patent: Apr. 15, 2008

(54) SPINAL TRACTION DEVICE AND METHOD

(76) Inventor: Ryan Meyers, 6007 Foxborough Square East, Brentwood, TN (US) 37027

( * ) Notice: Subject to any disclaimer, the term of this patent is extended or adjusted under 35 U.S.C. 154(b) by 290 days.

(21) Appl. No.: 11/039,263

(22) Filed: Jan. 19, 2005

(51) Int. Cl.
*A61F 5/00* (2006.01)
*A61G 15/00* (2006.01)
*A61H 1/00* (2006.01)

(52) U.S. Cl. ............................ 602/32; 602/33; 602/38; 602/39; 602/40; 128/845; 606/240; 606/241; 606/242; 606/243; 606/244; 606/245; 601/5

(58) Field of Classification Search .................. 602/32, 602/33, 35, 38, 39, 40; 128/845; 606/240–245; 601/5
See application file for complete search history.

(56) References Cited

U.S. PATENT DOCUMENTS 3,302,641 A * 2/1967 Berne et al. ................ 606/245
3,936,047 A * 2/1976 Brandt et al. ............... 482/146
5,031,898 A * 7/1991 Anthony ...................... 482/70
6,154,903 A * 12/2000 Wai-Chung .................... 5/632
6,237,172 B1 * 5/2001 Morgan, Sr. ................... 5/618
7,097,628 B1 * 8/2006 Baune ......................... 602/32
2005/0181917 A1 * 8/2005 Dayal ......................... 482/142

* cited by examiner

*Primary Examiner*—Patricia Bianco
*Assistant Examiner*—Tarla Patel
(74) *Attorney, Agent, or Firm*—Mark J. Patterson; Dennis H. Nunez; Waddey & Patterson

(57) ABSTRACT

A spinal traction/decompression device suitable for home or clinical treatment of lumbar and cervical spine pathology. The traction apparatus has a substantially flat upper body support that is moveable with respect to a fixed base. The upper body support is adapted to receive the upper torso of an individual leaning forward in a prone position while kneeling on a knee cushion. A pelvis/hip restraining portion holds the individual's lower torso in position with respect to the fixed base when the upper body support is moved. Lumbar traction may be induced by a user positioning their upper torso on the upper body support and moving it forward or backward with respect to the fixed base. The upper body support may also be divided into two independently moveable sections such that cervical traction can be induced in a neck region of a user. The traction force is preferably supplied by the individual pushing or pulling the upper body support forward with their arms. The upper body support may rotate, side bend, flex or extend with respect to the fixed base to alter the position of the spine when the lumbar traction is induced.

16 Claims, 2 Drawing Sheets

SPINAL TRACTION DEVICE AND METHOD

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to the field of medical spinal traction devices. It is well known in the prior art that a variety of spinal disorders can be treated by applying tension to the spine. The application of tension or traction to the spine serves to displace forces and relieve pressure of the spine and, thereby, facilitate the treatment a variety of conditions. Accordingly, a number of prior art lumbar and cervical traction devices have been developed for applying traction to the human spine. Unfortunately, these devices typically suffer from a number of drawbacks. For instance, many prior art devices are often bulky, heavy and difficult to install and/or use. In addition, the prior art devices are often very expensive and complex. As a result, they are typically not very portable and, thus, are more suitable for use in a hospital or clinical setting than they are for use in a home. Moreover, the lumbar and cervical traction devices that are intended for home use tend to be very limited in function and versatility. Prior art lumbar traction devices also tend to be uncomfortable and difficult to operate properly. In particular, lumbar traction units use belts or girdles that restrict breathing and have difficulty securing joints that are not being treated. Prior art lumbar and cervical traction devices which apply traction when the user is in the prone position are limited, if not rare.

In view of the above discussed deficiencies in the prior art, what is needed is a cost effective and improved device for use at home and in clinical settings that creates lumbar and cervical traction in an individual in the prone position.

BRIEF SUMMARY OF THE INVENTION

An embodiment of the present invention is directed toward a device for producing lumbar traction in an individual. The device includes a substantially horizontal body sled mounted on a fixed base such that the body sled can move in a substantially horizontal direction with respect to the fixed base. The body sled is adapted to support an upper torso of the individual when the individual is in a kneeling position next to the body sled with their upper torso positioned face down on the body sled. A facial opening is provided in the body sled such that the individual's face is received in the facial opening when the individual's upper torso is resting face down on the body sled. A cushioned knee support supports the individual's knees when the individual is positioned on the device. A thigh rest is positioned in a fixed relationship to the fixed base. The thigh rest prevents movement of the individual's lower torso with respect to the thigh rest. Leverage means apply a force to the body sled such that a spinal region of the individual is placed in traction. The leverage means preferably include a pair of push areas located on the thigh rest, at least one of a pair of hand grips mounted on a grip mount, a cable and pulley system and adaptable to use pumps or motors to apply forces. Most preferably, a rotational coupling couples the body sled to the fixed base such that the individual's upper torso can be rotated to the left or right with respect to the individual's lower torso.

A bending coupling couples the body sled to the fixed base such that the individual's upper torso can be bent to the left or right with respect to the individual's lower torso. A flexion and extension coupling couples the body sled to the fixed base such that the individual's upper torso can be slanted upward or downward with respect to the individual's lower torso. In an alternative embodiment, the body sled has a first portion and a second portion that are independently movable with respect to one another such that a user can produce cervical traction in their neck region.

Another embodiment of the present invention is directed toward a device for inducing lumbar traction in an individual. The device includes upper torso support means for substantially horizontally supporting an upper torso portion of the individual when the individual is in a kneeling position. The upper torso support means include a facial opening for receiving the face of the individual when the individual is lying face down on the upper torso support means. Lower torso restraining means restrain a lower torso portion of the individual when the individual is in the kneeling position. The lower torso restraining means are adjustable to accommodate individuals of different sizes. Traction means apply a stretching force to the upper torso support means such that lumbar traction is induced in the individual. The traction means preferably include a pair of push areas located on the thigh rest or pelvis bar that allow the individual to push their upper torso forward and/or a pair of hand grips adapted to be held in the individual's hands that allow the individual to pull their upper torso forward. The upper torso support means can be bent horizontally to the left or the right with respect to the lower torso support means. The upper torso support means can also be rotated to the left or right with respect to the lower torso means. Finally, the upper torso means can be rotated up or down with respect to the lower torso restraining means such that flexion and extension are respectively induced in the individual's spine when the upper torso means is rotated up or down. In an alternative embodiment, the upper torso support means are divided into a head portion and a torso portion that can be moved independently of one another to induce cervical traction in a neck region of an individual.

Yet another embodiment of the present invention is directed toward a device for producing lumbar traction in an individual. The device includes a moveable table mounted on a fixed based wherein the individual kneels such that the individual's upper torso rests face down on the moveable table and the individual's lower torso is secured to the fixed base. Lumbar traction is then induced in the individual's spine by moving the moveable table with respect to the fixed base. The moveable table is preferably moved by the individual physically pushing or pulling the moveable table forward. Most preferably, hand placement areas or hand grips on the thigh rest are provided that allow the individual to push their upper torso forward. The moveable table may also rotate or bend with respect to the fixed base and be adjusted to provide flexion and extension. A traction force measuring means and display means are provided for measuring and displaying a traction force applied to the individual's spine. In an alternative embodiment, the moveable table is divided into at least two sections that can be independently moved with respect to one another to produce cervical traction in a neck region of a user.

DETAILED DESCRIPTION OF THE INVENTION

Figure 2:
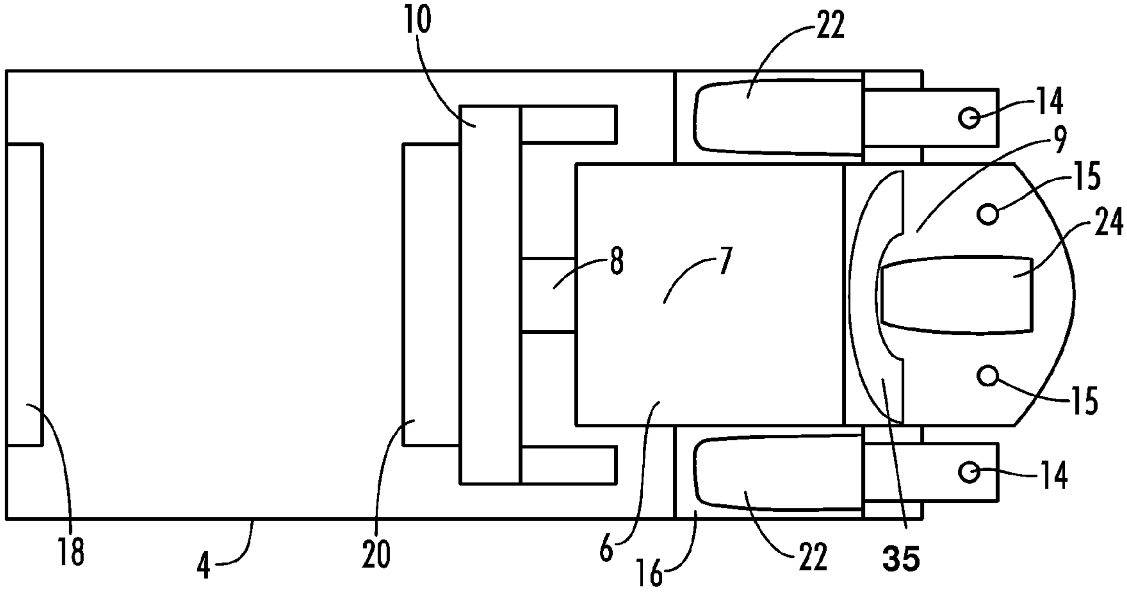
FIG. 2 is a top view of a preferred embodiment of the present invention.
Figure 1:
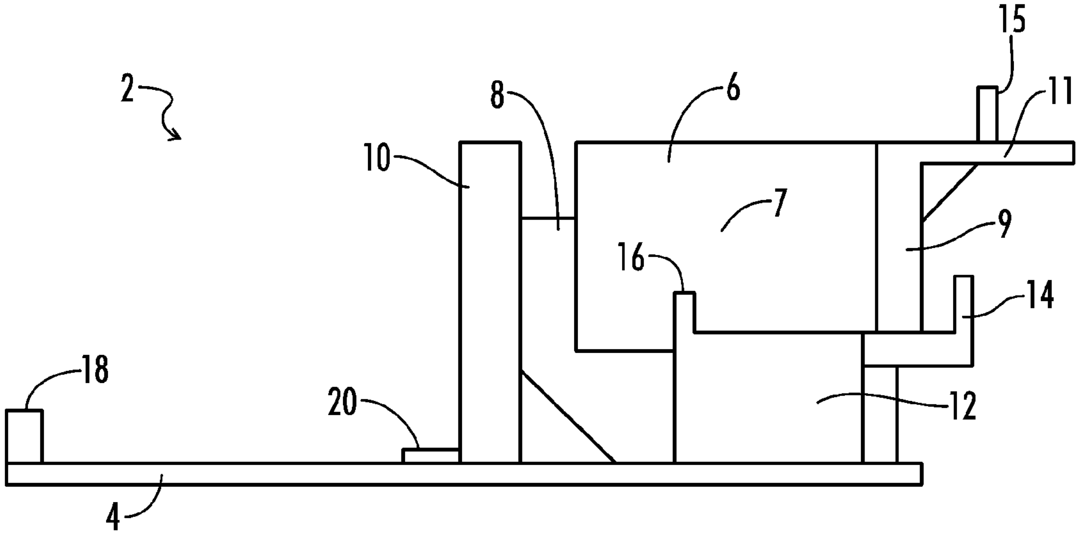
FIG. 1 is a side view of a preferred embodiment of the present invention.

Referring now to FIGS. 1 and 2, a preferred embodiment of the present lumbar traction device 2, for treating back problems associated with compression of the spine is shown. The lumbar traction device 2 is mounted on a substantially flat base 4 that is designed to rest on a substantially flat surface such as a floor. A moveable body sled 6 for supporting the upper torso of a user is slideably coupled to a sled support 8 with extension glides, tracks, or bars that allow for forward and backward horizontal motion. Alternatively, rockers or gliders can be used to provide forward and backward movement to the body sled 6 in a manner similar to that used in conjunction with a rocking chair.

The sled support 8 is firmly secured to the flat base 4. A cushioned head support 11 having a facial opening 24 for receiving the face of a user lying face down on the body sled 6 extends from the body sled 6. A thigh rest 10 for restraining the lower torso of a user is positioned in close proximity to the sled support 8. Preferably, the thigh rest 10 is upwardly or downwardly adjustable to conform to the body shape of a user and the top surface of the thigh rest 10 is cushioned for added comfort. A grip mount 12 is positioned on the base 4 in fixed relationship to the sled support 8. The grip mount 12 has a lower hand grip 14 that is positioned so as to approximately align with the shoulders of a user resting face down on the body sled 6. An elbow support 16 is provided on the grip mount 12 to provide additional leverage for stretching the spine. An arm cushion 22 is preferably positioned on the grip mount 12 to provide a comfortable resting position for the user's forearms. A foot stop 18 and a knee cushion 20 are also mounted on the base 4. The foot stop 18 helps secure an individual's lower torso between the pelvis bar 10 and the foot stop 18 while the knee cushion 20 simply provides a comfortable surface on which a user can position their knees when in a kneeling position. Preferably, both the foot stop 18 and the knee cushion 20 are adjustable so as to accommodate individuals of a various different sizes With continuing regard to FIGS. 1 and 2, the operation of a preferred embodiment of the present invention will now be explained. When positioned on the device, the user is in a kneeling and prone position with the hips and knees flexed at approximately 90 degrees. More particularly, to stretch the spine and undergo lumbar traction, the user kneels with their knees resting on the knee cushion 20. The bottoms of the individual's feet are then placed into contact with the foot support 18. A strap (not shown) may be used to secure the individual's feet to the foot support 18 and/or the thigh rest 10 and/or the body sled 6 if desired. Once the user's lower torso is positioned between the foot support 18 and the thigh rest 10 with their knees resting on the knee cushion 20, the user bends forward such that their upper torso rests against the body sled 6 and their face is looking down through the facial opening 24. A forward movement of the body sled 6 can be produced both using and not using the grip mounts 12. Not using the grip mounts 12, the user's hands are securely placed on the thigh rest 10 with the elbows extended or slightly flexed. Using the grip mounts 12, the user's forearms are then positioned on the arm cushions 22 on the top surface of the grip mount 12 with the elbows flexed and the user's hands are securely placed around the lower hand grips 14. By either pushing off the thigh rest 10, not using the grip mounts 12, or by pulling on the lower hand grips 14 and pushing against the arm cushions 22, using the grip mounts 12, with their feet secured with the foot stop 18 and thighs firmly pressed against the thigh rest 10, in the same manner a person would push off arm rests when sitting in a chair to stand up or push off a seat with no arm rests to lift their body off the seat, the user can cause the body sled 6 to slide along the sled support 8 away from the thigh rest 10.

As the body sled 6 moves away from the thigh rest 10, the upper torso of the user lying prone on the moving body sled 6 moves forward. With the pelvis stationary and secured and the upper torso moving forward, lumbar traction is produced in the spine of the user. This requires little physical effort, especially when the user's elbows are fully extended and locked. In such a situation, the patient or user can maintain the lumbar traction for prolonged periods without expending a large amount of effort. Thus, the device of the present invention provides a simple and cost effective means for inducing lumbar traction in a person in a kneeling/prone position.

In an alternative embodiment, the device 2 is adapted to allow a user to induce cervical traction. In such an embodiment, the body sled 6 is divided into a back section 7 and a front section 9. The division between the sections 7 and 9 is positioned approximately where the top of the shoulders or base of the neck of a user will rest when the user is positioned on the body sled 6. Thus, sections 7 and 9 form a lower body sled 7 and a head sled 9. Both sections 7 and 9 are independently moveable with respect to one another and able to be locked in place. An adjustable head strap 35 (FIG. 2) is provided on the head sled 9 to secure the users head behind the occiput.

There are two primary ways to produce cervical traction using the alternative embodiment. First, the head sled 9 may be locked in position so that it is stationary. The user then either pulls on the thigh rest 10 or pushes on the lower hand grips 14, elbow rests 16, and/or arm rests 22 to the move the lower body sled 7 in a backward motion. Conversely, the lower body sled 7 can be locked into position such that it is stationary. The user then pushes on the upper hand grips 15 positioned on the head sled 9 such that the head sled 9 moves forward and produces cervical traction.

The power to place the lumbar spine in traction using the embodiments of FIGS. 1 and 2 can come from a number of sources. The lumbar traction device is preferably powered by the individual or patient using their arms/hands to push off the stationary thigh rest 10; using their arms/elbows/hands to push off the rests 12, 16 and 22; or placing their arms/hands out front and/or overhead and pulling on the lower hand grips 14. Alternatively, other devices can be used to move the body sled 6 forward to produce traction; a crank and/or pulley system whereby a user pulls on chains/ropes/straps, a rocker or glider system (rocking chair method), as well as motors and air, pneumatic or hydraulic pumps. Once lumbar traction has been applied to the spine, a locking device may be used to secure the body sled 6 in position and, thus, lessen the force that must be applied through the arms.

The above described preferred embodiment of the present lumbar traction device provides a number of advantages over prior art lumbar traction devices. First, the preferred embodiment may be constructed from a few relatively simple wooden, plastic or metal parts with no powered or motorized components. Thus, a lumbar traction device constructed in accordance with a preferred embodiment of the present invention is relatively inexpensive to construct. The embodiment of FIGS. 1 and 2 is also small and light enough to be easily portable, especially when it is constructed out of light weight materials. Furthermore, the device does not require any assistance to use and, thus, is fully capable of being used by a single, individual. Thus, it is particularly well suited for use in the privacy of one's own home. Nevertheless, if desired, the device could also easily be implemented as a more robust, stationary table version for clinical use by an individual under the supervision of a professional.

A preferred embodiment of the present invention stabilizes non-treated joints better to apply more effective traction through the lumbar spine. This is due to the fact that the forces are transferred through the hip joint which is the most stable joint in the body. Prior home and clinical lumbar traction units are only used with the lumbar spine in a neutral position and offer zero degrees of lumbar flexion and extension. Minimal lumbar flexion occurs when an individual is in a supine position with the knees and hips flexed. Therefore, the ability of embodiments of the present invention to provide lumbar flexion and extension to an individual in a prone position represents a substantial improvement upon the prior art.

Figure 3:
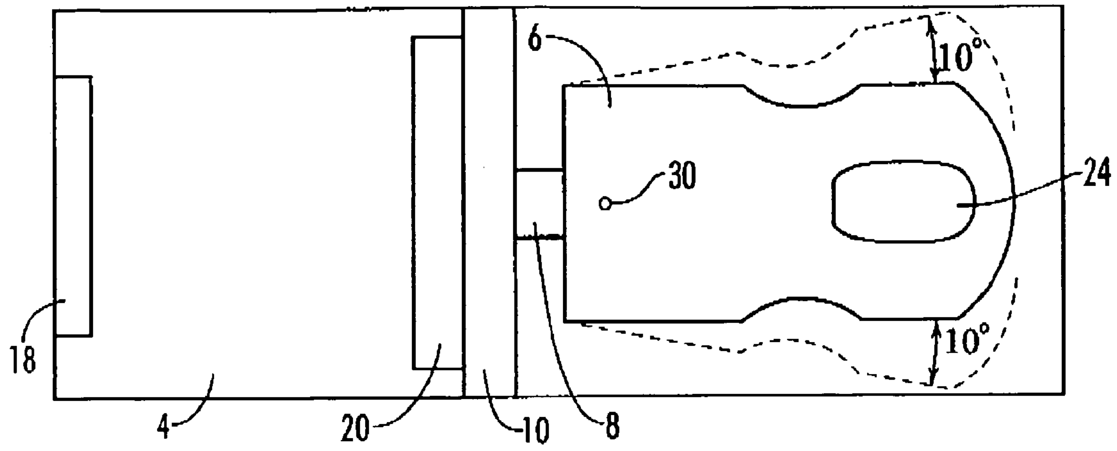
FIG. 3 is a pictorial representation of a side bending range of movement provided by a preferred embodiment of the present invention.
Figure 4:
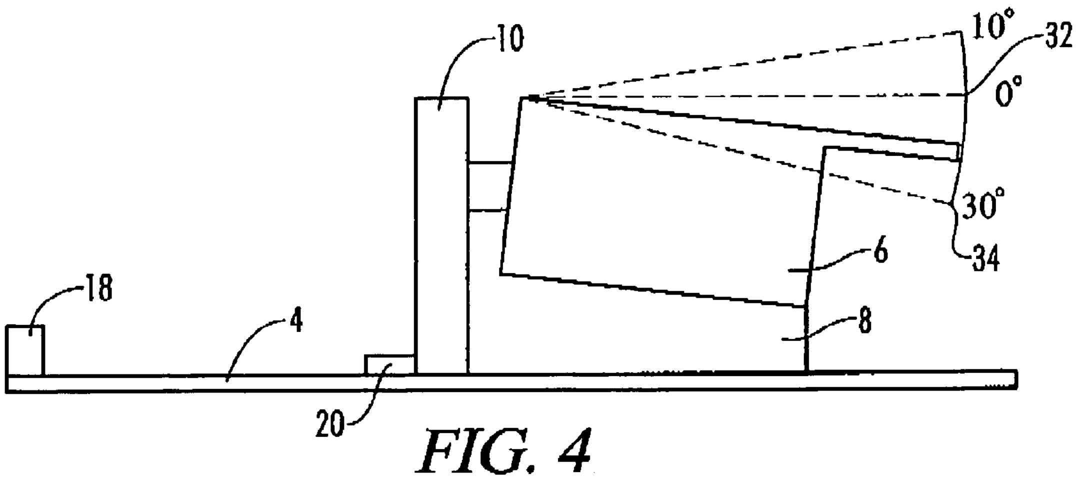
FIG. 4 is a pictorial representation of the flexion and extension movements provided by a preferred embodiment of the present invention.
Figure 5:
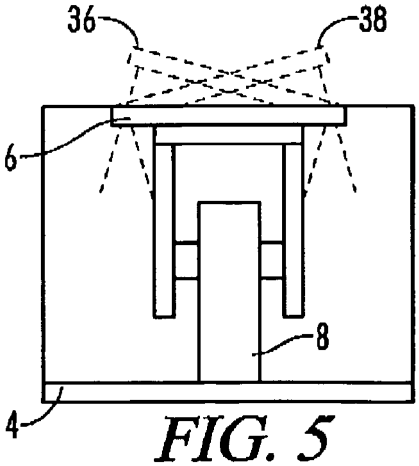
FIG. 5 is an illustration of the rotational range of movement provided by a preferred embodiment of the present invention.

To provide increased utility and flexibility, the preferred embodiments of the present invention set forth in FIGS. 3, 4 and 5 offer lumbar traction in combination with three planes of movement, i.e., side bending as shown in FIG. 3, flexion and extension as shown in FIG. 4, and rotational as set forth in FIG. 5.

With regard to FIG. 3, varying degrees of side bending can be obtained by allowing the sled 6 to rotate about a pivot point 30. Most preferably, the sled rotates in a horizontal plane to provide up to 100% of the user's available side bending ability to either the right or the left. This is beneficial in that it allows the spine to be more precisely positioned and stretched to accommodate the particular symptom relief of the individual being treated.

With particular regard to FIG. 4, due to the vertical rotational movement of the sled 6, traction can be performed with the lumbar spine in either a neutral alignment 32 with 0 degrees flexion/extension or with an offset alignment 34 that provides varying degrees of flexion/extension. Most preferably, the lumbar traction device provides up to 100% of user's extension and flexion ability. The ability to provide flexion and extension in combination with lumbar traction is beneficial in that it allows the spine to be more precisely positioned and stretched to accommodate the particular symptom relief of the individual being treated.

A preferred embodiment of the present invention also provides varying degrees of lumbar spinal rotation in a vertical plane as shown in FIG. 5. By rotating to the right 36 or left 38 in a vertical plane, the sled 6 can accommodate up to 100% of a typical individual's lumbar spinal rotation. The ability to rotate the spine while inducing lumbar tension in the spine is beneficial in that it allows the spine to be more precisely positioned and stretched to accommodate the particular symptom relief of the individual being treated.

The lumbar traction forces provided by the various embodiments can be measured by a variety of methods if desired. For example, scales may be placed on the hand placement areas on the pelvis block 10 and the recorded forces added together to determine a traction force in pounds. A torsion spring or a torque measuring device could also be utilized to provide an approximation of the traction forces being applied to the spine of a patient or user. Such detailed measurements may be particularly useful when using the present invention in a clinical setting such that a consistent and uniform amount of lumbar traction can be applied to a patient.

The treatment time required when using an embodiment of the present invention varies with a variety of factors including whether or not constant or intermittent traction is applied. In a most preferred embodiment, the device has a digital read out whereby a user can monitor the time spent in traction and the amount of force applied. The digital read out is preferably positioned such that a user can read it when their face is placed in facial opening.

Although there have been described particular embodiments of the present invention of a new and useful Spinal Traction Device and Method, it is not intended that such references be construed as limitations upon the scope of this invention except as set forth in the following claims.

What is claimed is:

1. A device for producing lumbar traction on a spinal region of an individual having an upper and a lower torso positioned on the device in a kneeling position, the device comprising:

a base;

a thigh rest extending upward from the base in a fixed position to engage the thighs of the individual and to prevent forward movement of the lower torso of the individual in the kneeling position, the thigh rest being fixed at a location with respect to the base; and a body sled extending forward from the thigh rest to support the upper torso of the individual in the kneeling position, the body sled being movably mounted on the fixed based such that a force manually applied by the individual moves the body sled away from the thigh rest in at least a horizontal direction relative the base, thereby producing lumbar traction.

2. The device of claim 1 further comprising a rotational coupling for coupling said body sled to said base such that said individual's upper torso can be rotated to the left or right with respect to said individual's lower torso.

3. The device of claim 1 further comprising a side bending coupling for coupling said body sled to said base such that said individual's upper torso can be bent to the left or right with respect to said individual's lower torso.

4. The device of claim 1 further comprising a flexion and extension coupling for coupling said body sled to said base such that said individual's upper torso can be slanted upward or downward with respect to said individual's lower torso.

5. The device of claim 1 wherein said body sled further comprises a facial opening such that said individual's face is received in said facial opening when said individual's upper torso is resting face down on said body sled.

6. The device of claim 1 wherein said body sled has a first portion supporting the torso and a second portion supporting the head that are independently movable with respect to one another, the body sled further comprising a head strap and hand grips attached to the second portion such that a user can produce cervical traction in their neck region by pushing on the hand grips.

7. A device for producing lumbar traction on a spinal region of an individual having an upper and a lower torso positioned on the device in a kneeling position, the device comprising:

a base;

a movable table for supporting the upper torso of the individual in the kneeling position, the movable table being mounted on the base so that the table is movable in at least a horizontal direction relative the base; and a thigh restraint extending upward from the base in fixed position for restraining the lower torso of the individual in the kneeling position, the thigh restraint having a fixed position with respect to the base wherein applying a manual force with respect to the table moves the table away from the thigh restraint thereby creating traction on the spinal region of the individual in the kneeling position.

8. The device of claim 7 further comprising hand grips for pulling the upper torso forward.

9. The device of claim 7 wherein said moveable table rotates or bends with respect to said base.

10. The device of claim 7 wherein said moveable table is divided into at least two sections that can be independently moved with respect to one another to produce cervical traction in a neck region of a user.

11. A method of creating traction in a spinal region of an individual, the method comprising:

(a) placing an upper torso of the individual on a table movably mounted on a base wherein the individual is in a kneeling position;

(b) restraining the lower torso of the individual in the kneeling position against a thigh rest, the thigh rest being maintained in a fixed position to maintain the lower torso in a fixed position; and (c) moving the table away from the thigh rest while the individual is in the kneeling position.

12. The method of claim 11, wherein step (c) further comprises bending the table to the left or right with respect to the thigh rest.

13. The method of claim 11, wherein step (c) further comprises rotating the table up or down with respect to the thigh rest.

14. The method of claim 11, wherein step (a) further comprises lying the individual face down on the table wherein a face of the individual is received in a facial opening defined by the table.

15. The method of claim 11, wherein step (c) further comprises providing a pair of hand grips wherein the individual pulls on the hand grips to move the table.

16. The method of claim 11, further comprising inducing cervical traction on a neck of the individual by moving a front section of the table relative to a back section of the table.

* * * * *